(12) United States Patent
Gerder et al.

(10) Patent No.: US 7,647,926 B2
(45) Date of Patent: Jan. 19, 2010

(54) BREATHING GAS TUBE FOR A RESPIRATOR

(75) Inventors: Henning Gerder, Lübeck (DE); Andreas Krause, Lübeck (DE); Götz Kullik, Lübeck (DE)

(73) Assignee: Drägerwerk AG, Lübeck (DE)

( * ) Notice: Subject to any disclaimer, the term of this patent is extended or adjusted under 35 U.S.C. 154(b) by 1148 days.

(21) Appl. No.: 10/737,202

(22) Filed: Dec. 16, 2003

(65) Prior Publication Data
US 2004/0182392 A1 Sep. 23, 2004

(30) Foreign Application Priority Data
Mar. 22, 2003 (DE) .................................. 103 12 881

(51) Int. Cl.
*A61M 11/00* (2006.01)
(52) U.S. Cl. .................... 128/204.22; 128/204.18
(58) Field of Classification Search ............ 128/204.18, 128/204.21, 204.22, 204.23, 204.17, 911, 128/912, 203.12, 203.16; 600/529, 532, 600/538, 300
See application file for complete search history.

(56) References Cited

U.S. PATENT DOCUMENTS

| 4,323,064 | A | | 4/1982 | Hoenig et al. | |
|---|---|---|---|---|---|
| 6,044,843 | A | * | 4/2000 | O'Neil et al. | 128/204.23 |
| 2001/0017134 | A1 | * | 8/2001 | Bahr | 128/204.18 |
| 2003/0236015 | A1 | * | 12/2003 | Edirisuriya et al. | 439/191 |
| 2004/0182386 | A1 | * | 9/2004 | Meier | 128/203.12 |

FOREIGN PATENT DOCUMENTS

EP 0 201 985 11/1986

* cited by examiner

*Primary Examiner*—Steven O Douglas
(74) *Attorney, Agent, or Firm*—McGlew and Tuttle, P.C.

(57) ABSTRACT

A connection of a sensor to a respirator/ventilator is provided without individual cable connections having to be led from the respirator to the sensor. A signal line (18) extends along the breathing gas tube (2) and is designed to transmit signals of the sensor (16) to the respirator. A contactless interface (17) is provided between the signal line (18) and the sensor (16).

21 Claims, 2 Drawing Sheets

BREATHING GAS TUBE FOR A RESPIRATOR

FIELD OF THE INVENTION

Sensors, with which measurements are performed in the breathing gas flow in the vicinity of the test subject, are used to control respirators (or ventilators or other breathing equipment). The measurement of the breathing gas volume flow in the vicinity of the test subject is thus part of many contemporary respirators, e.g., in medicine. Respirators are used in medicine predominantly as mechanical respirators or ventilators for respirating or ventilating patients. The task of the sensors is to detect breathing gas parameters in order to adjust the respirator to the breathing gas demand of the patient as optimally as possible. There also are respiratory protective devices in the form of a closed gas mask and respiratory protective devices or fan-operated breathing equipment. The task of these respirators is to supply a user with a sufficient amount of breathing gas during a mission.

BACKGROUND OF THE INVENTION

A respirator (ventilator) for medical applications has become known from U.S. Pat. No. 4,323,064. An inspiration tube and an expiration tube are connected to one another via a Y-piece, with a flow sensor and a respiration tube being connected to the end of the Y-piece pointing toward the patient. The flow sensor detects the gas flow both during the inspiration phase and during the expiration phase. The electric contacting of the flow sensor is achieved via a cable connection, which extends from the respirator to the flow sensor.

The drawback of the prior-art respirator is that the cable connection must be led separately to the evaluating device from the breathing gas tubes. If other parameters of the gas, such as the breathing gas temperature, the $O_2$ or $CO_2$ concentration, are also measured, besides the gas flow, additional cable connections are necessary, which compromise care procedures performed at the patient due to the sensors being arranged close to the patient.

EP 201 985 A1 discloses a breathing gas tube, which has a resistance wire extending helically along the tube. A sensor wire, which is used for contacting temperature sensors, which are arranged at the ends of the breathing gas tube, is led in parallel to the resistance wire.

The drawback of the prior-art breathing gas tube is that sensors which are located at adjacent connectors connected to the breathing gas tube must be connected to the sensors via separate electric patch plugs. Since breathing gas tubes are regularly sterilized or disinfected in clinical practice, such patch plugs are subject to high wear and, moreover, contact resistances may develop at the contact points, and these resistances may distort the often very low measured signal voltages. In addition, the number of plugging cycles is limited in electric patch plugs, so that the entire breathing gas tube must be replaced after a certain duration of use because of contacts that have become unfit for use.

SUMMARY OF THE INVENTION

The basic object of the present invention is to improve a breathing gas tube such that a signal interface for a sensor means that can be connected to the breathing gas tube is insensitive to processing measures.

A breathing gas tube at a respirator (ventilator) for supplying a test subject with breathing gas is provided with a sensor means at an end of the breathing gas tube facing away from the respirator. A signal line extends along the breathing gas tube and is designed to transmit signals of the sensor means to the respirator. A contactless interface is provided between the signal line and the sensor means.

The advantage of the present invention is essentially that, on the one hand, a separate cable connection extending in addition to the breathing gas tube is avoided due to the combination of a signal line for sensor data, which extends along the breathing gas tube, with a contactless interface between the breathing gas tube and the sensor means, and, on the other hand, that the sensor data can be directly transmitted to the respirator via the contactless interface and the breathing gas tube. For example, an optical interface, which is characterized in that it is especially insensitive to external disturbing effects, especially magnetic fields, is suitable for use as a contactless interface. For actuating the optical interface, the sensor means has an energy supply of its own, e.g., in the form of a battery. The field of use of the present invention is not limited to respirators or ventilators for medical applications, but it also covers respiratory protective devices.

The sensor data are advantageously transmitted at the optical interface via one or more fiberoptic waveguides acting as a signal line. The fiberoptic waveguide is either bonded to the breathing gas tube or directly vulcanized to the tube material. Optical interfaces are thus present at both ends of the breathing gas tube.

The signal line is advantageously designed as a two-wire or multiwire line. The two-wire line makes possible a so-called half-duplex operation here, in which control and measured data are transmitted alternatingly. A controlled half-duplex operation is possible in the case of a three-wire line. A four-wire line makes possible full duplex operation, which is especially advantageous when the sensor means contains a plurality of sensors and a plurality of different sensor data must consequently be transmitted.

The signal transmission between the respirator and the sensor means advantageously takes place bidirectionally via a data BUS system. It is thus possible to transmit the data of different sensors within the sensor means via a single data line. A two-wire line is preferably suitable for use as the data line. However, more than two lines may also be led helically along the tube.

It is especially advantageous to additionally use the two-wire line as a tube heater. The simultaneous use of the two-wire line as a data line and as a tube heater offers the user the advantage that the interruption of the two-wire line can be immediately recognized from the fact that the breathing gas tube is not heated any longer.

The contactless interface is advantageously designed as a first inductive interface. Besides the measured data, energy can also be transmitted via the first inductive interface from the respirator to the sensor means, so that no separate energy supply needs to be provided there any longer.

The sensor means is advantageously designed as a single sensor means or as a combination for measuring temperature, humidity, gas flow, gas concentration or pressure.

The transmission of sensor signals is an advantageous use of a contactless interface between a breathing gas tube and a sensor means. The contactless interface may be a first inductive interface. The first inductive interface may be provided to transmit a supply voltage to the sensor means in addition to the signals. The contactless interface may be an infrared interface.

The sensor means may be designed as an individual sensor means or as a combination for the measurement of temperature, humidity, flow, gas concentration or pressure.

A second inductive interface may be provided between the breathing gas tube and the respirator.

According to another aspect of the invention, a process is provided for using a contactless interface between a breathing gas tube and a sensor means for transmitting sensor signals.

Exemplary embodiments of the present invention are shown in the figures and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
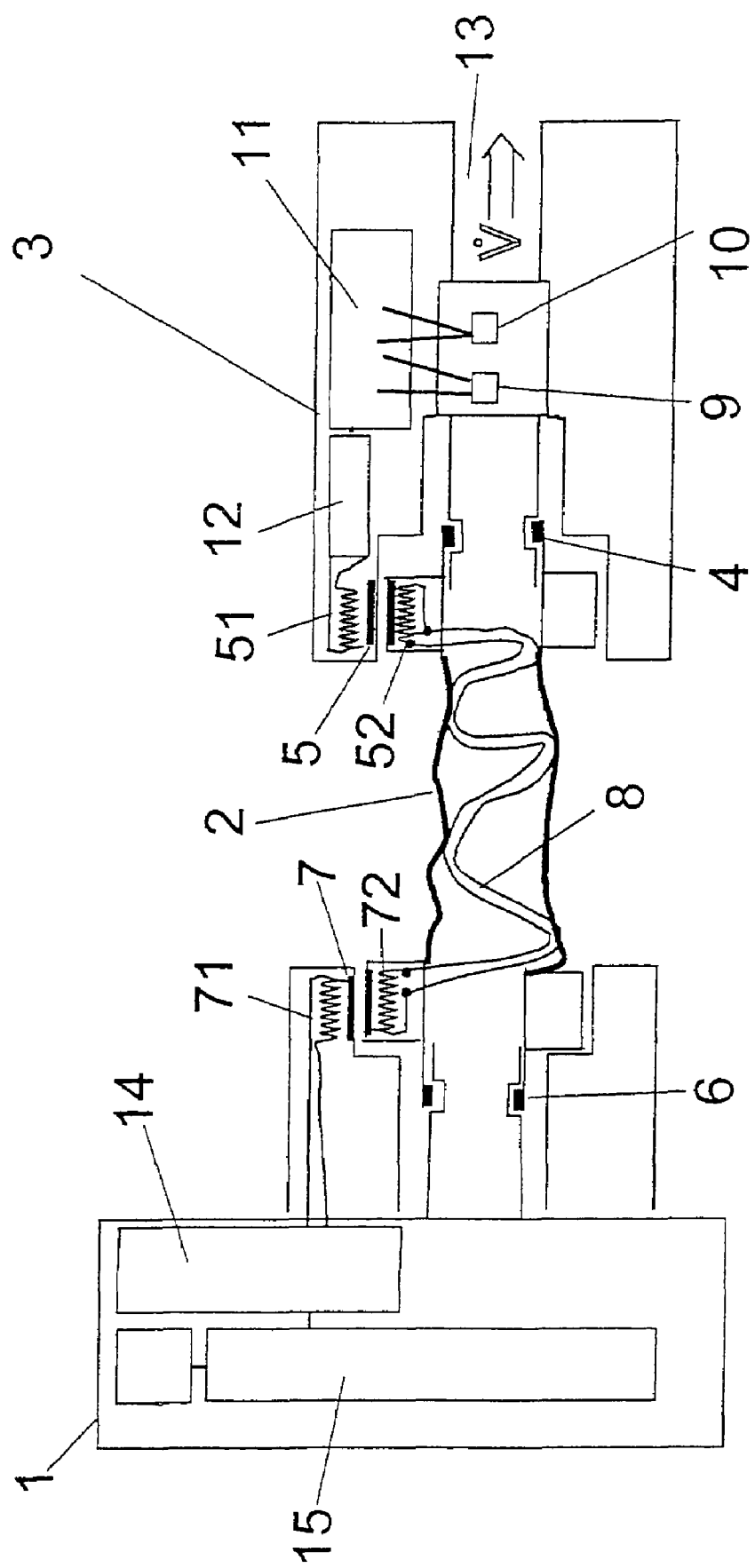
FIG. 1 is a sensor means connected to a respirator via a breathing gas tube.

Referring to the drawings in particular, FIG. 1 schematically shows a respirator or ventilator 1, which is connected to a sensor means 3 via a breathing gas tube 2. The breathing gas tube 2 has a first tube coupling 4 with a first inductive interface 5 at the sensor means 3 and a second tube coupling 6 with a second inductive interface 7 at the respirator 1. The first inductive interface 5 is divided into a sensor interface 51 connected to the sensor means 3 and a first tube interface 52 arranged at the breathing gas tube 2. The second inductive interface 7 correspondingly has a second tube interface 72 and a respirator interface 71. The tube interfaces 52, 72 are connected to one another via a two-wire line 8 extending along the breathing gas tube 2. A temperature sensor 9 and a flow sensor 10, which are arranged in the area of the first tube coupling 4 within the breathing gas flow, are located at the sensor means 3.

An electronic circuit 11 with a microprocessor is connected to both the sensor interface 51 and the sensors 9, 10. The electronic circuit 11 processes the measured signals and generates a data protocol, which is transmitted via the interfaces 5, 7 to the respirator 1. An energy supply block 12 connected to the electronic circuit 11 is used to supply the electronic circuit 11 with power. Via the two-wire line 8, the energy supply block 12 receives an alternating voltage, which feeds a battery, not shown specifically in FIG. 1, which is located in the sensor means 3, after rectification. The output 13 of the sensor means 3 is connected to a test subject or user, likewise not shown in FIG. 1.

The respirator 1 contains a signal processing unit 14, which is connected to the respirator interface 71 and a central computing and control unit 15 of the respirator 1. The signal processing unit 14 generates a data protocol for the bidirectional data communication between the sensor means 3 and the respirator 1 and additionally supplies the alternating voltage, which is fed into the sensor means 3 via the first inductive interface 5. The central computing and control unit 15 receives the measured values for the breathing gas temperature and the breathing gas flow, which are detected by the sensors 9, 10, from the data protocol supplied by the signal processing unit 14.

Figure 2:
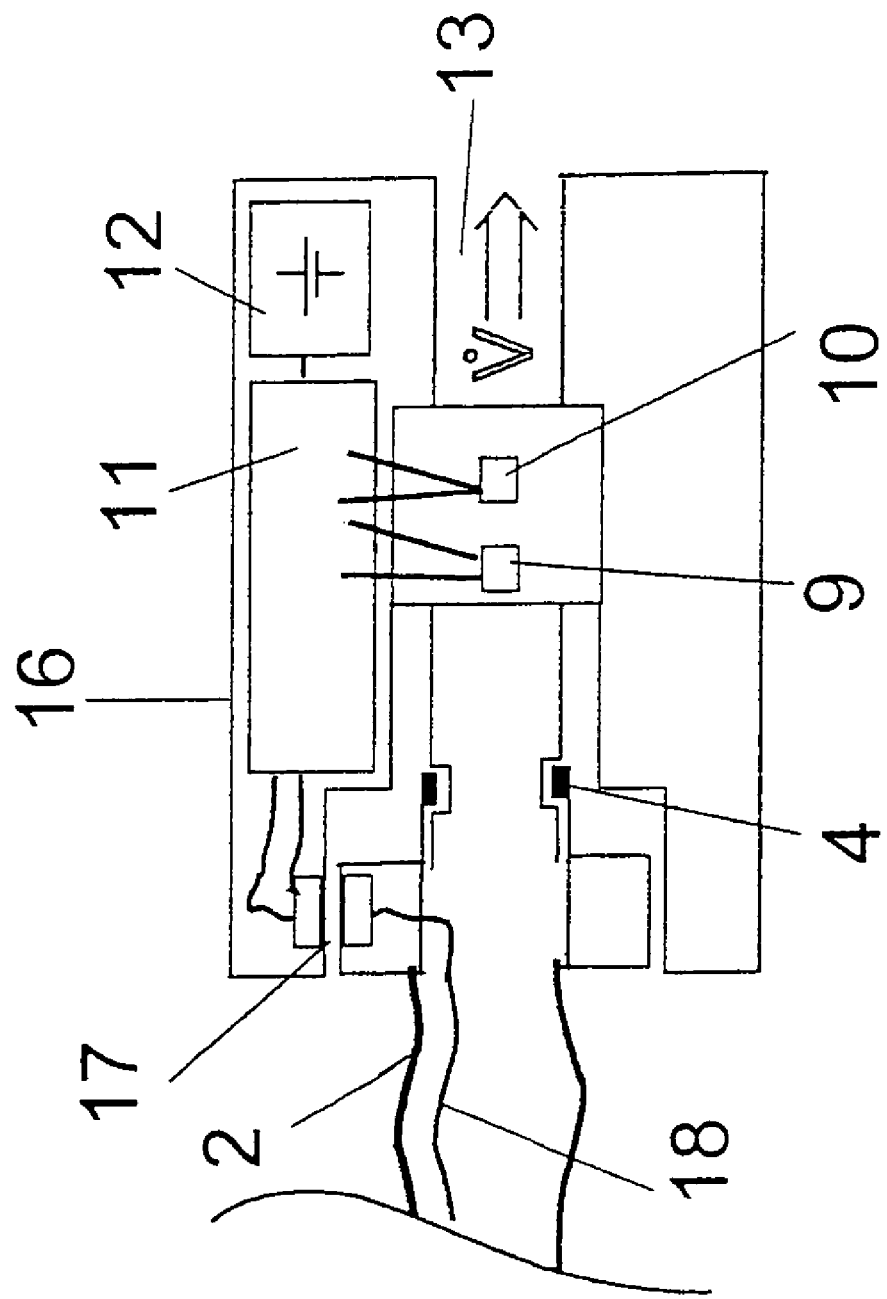
FIG. 2 is an alternative embodiment of a sensor means.

FIG. 2 shows an alternative embodiment of a sensor means 16, which differs from the sensor means 3 according to FIG. 1 in that an infrared interface 17 is provided instead of a first inductive interface 5. Identical components are designated by identical reference numbers as in FIG. 1. The infrared interface 17 makes possible a bidirectional data exchange via a fiberoptic waveguide 18 along the breathing gas tube 2. The infrared interface 17 is characterized by its insensitivity to magnetic stray fields. Since no energy can be transmitted via the infrared interface 17, the energy supply block 12 contains button cells or a battery chargeable from an external site.

While specific embodiments of the invention have been shown and described in detail to illustrate the application of the principles of the invention, it will be understood that the invention may be embodied otherwise without departing from such principles.

What is claimed is:

1. A respirator breathing gas tube for supplying a user with breathing gas, the breathing tube, comprising:
   a sensor means at an end of the breathing gas tube facing away from the respirator;
   a signal line extending along the breathing gas tube and designed to transmit signals of the sensor means to the respirator;
   a contactless interface between the signal line and the sensor means.

2. A breathing gas tube in accordance with claim 1, wherein the signal line comprises a fiberoptic waveguide.

3. A breathing gas tube in accordance with claim 1, wherein the signal line is a two-wire line.

4. A breathing gas tube in accordance with claim 1, wherein the signal transmission between the respirator and the sensor means takes place bidirectionally via a data transfer.

5. A breathing gas tube in accordance with claim 3, wherein the two-wire line is additionally designed as a tube heater.

6. A breathing gas tube in accordance with claim 3, wherein the contactless interface includes a first inductive interface.

7. A breathing gas tube in accordance with claim 6, wherein the first inductive interface is designed to transmit a supply voltage to the sensor means in addition to the signals.

8. A breathing gas tube in accordance with claim 1, wherein the contactless interface is an infrared interface.

9. A breathing gas tube in accordance with claim 1, wherein:
   the breathing tube has a first end adjacent the sensor means and a second end, a respirator is arranged adjacent said second end, said signal line extends along said breathing tube from said first end to said second end, the sensor means is designed as an individual sensor means or as a combination for a measurement of temperature, humidity, flow, gas concentration or pressure.

10. A breathing gas tube in accordance with claim 1, wherein another contactless interface is provided between the breathing gas tube and the respirator.

11. A process for using respiration system with a respirator, the process comprising the steps of:
   providing a sensor means for sensing breathing gas characteristics;
   providing a breathing gas tube;
   providing a contactless interface between the breathing gas tube and the sensor for transmitting sensor signals.

12. A process according to claim 11, further comprising:
   disposing the sensor means at an end of the breathing gas tube facing away from the respirator;
   providing a signal line extending along the breathing gas tube and transmitting signals of the sensor means to the respirator with the contactless interface being provided between the signal line and the sensor means.

13. A process according to claim 12, wherein the signal line comprises one of a fiberoptic waveguide and a two-wire line.

14. A process in accordance with claim 11, wherein the signal transmission between the respirator and the sensor means takes place bidirectionally via a data transfer.

15. A process in accordance with claim 13, wherein the two-wire line additionally heats the breathing gas tube.

16. A process in accordance with claim 13, wherein the contactless interface includes one of an inductive interface and an infrared interface.

17. A process in accordance with claim 11, wherein the sensor means measures one or more of temperature, humidity, gas flow, gas concentration or gas pressure.

18. A respiration system, comprising:
a respirator/ventilator;
a breathing gas tube for supplying a user with breathing gas, the breathing tube being connected to said respirator/ventilator at a proximal end and said breathing gas tube having a distal end;
a sensor at a distal end of said breathing gas tube;
a signal line extending along said breathing gas tube for transmitting signals of the sensor to said respirator/ventilator;
a contactless interface between said signal line and said sensor.

19. A respiration system in accordance with claim 18, wherein the signal line comprises one of a fiberoptic waveguide and a two-wire line establishing bidirectionally signal transmissions between said respirator/ventilator and said sensor.

20. A respiration system in accordance with claim 19, wherein the two-wire line is additionally designed as a tube heater.

21. A respiration system in accordance with claim 18, wherein another contactless interface is arranged between said breathing gas tube and said respirator/ventilator, the contactless interfaces includes one of an inductive interface and an infrared interface.

* * * * *